United States Patent [19]

French et al.

[11] 4,201,764

[45] May 6, 1980

[54] SPRAY DISINFECTANT AEROSOL

[75] Inventors: Floyd R. French; Janet N. Paige, both of Midland, Mich.

[73] Assignee: Calvin N. Goeders, Midland, Mich.

[21] Appl. No.: 661,090

[22] Filed: Feb. 25, 1976

Related U.S. Application Data

[63] Continuation-in-part of Ser. No. 351,210, Apr. 16, 1973, abandoned, which is a continuation-in-part of Ser. No. 323,754, Jan. 15, 1973, abandoned.

[51] Int. Cl.[2] .......... A61L 9/04

[52] U.S. Cl. .......... 424/45; 424/343

[58] Field of Search .......... 424/45, 343

[56] References Cited

U.S. PATENT DOCUMENTS

| | | | |
|---|---|---|---|
| 3,102,101 | 8/1963 | Hawley | 252/305 |
| 3,282,776 | 11/1966 | Kitzke et al. | 424/45 |
| 3,287,214 | 11/1966 | Taylor et al. | 424/45 |
| 3,650,981 | 3/1972 | Inouye et al. | 424/45 X |

OTHER PUBLICATIONS

Remington–Pharmaceutical Sciences, 13th ed., pp. 652–653, (1965).

Burrows, "Textbook of Microbiology", p. 220, (1963).

*Primary Examiner*—Leonard Schenkman

[57] ABSTRACT

A pressurized single phase disinfectant composition consists essentially of from 10 to 45 weight percent water and from 53 to 88 weight percent ethanol the balance being propane with all such compositions restricted to those falling within the area PQLO of the accompanying graph.

11 Claims, 1 Drawing Figure

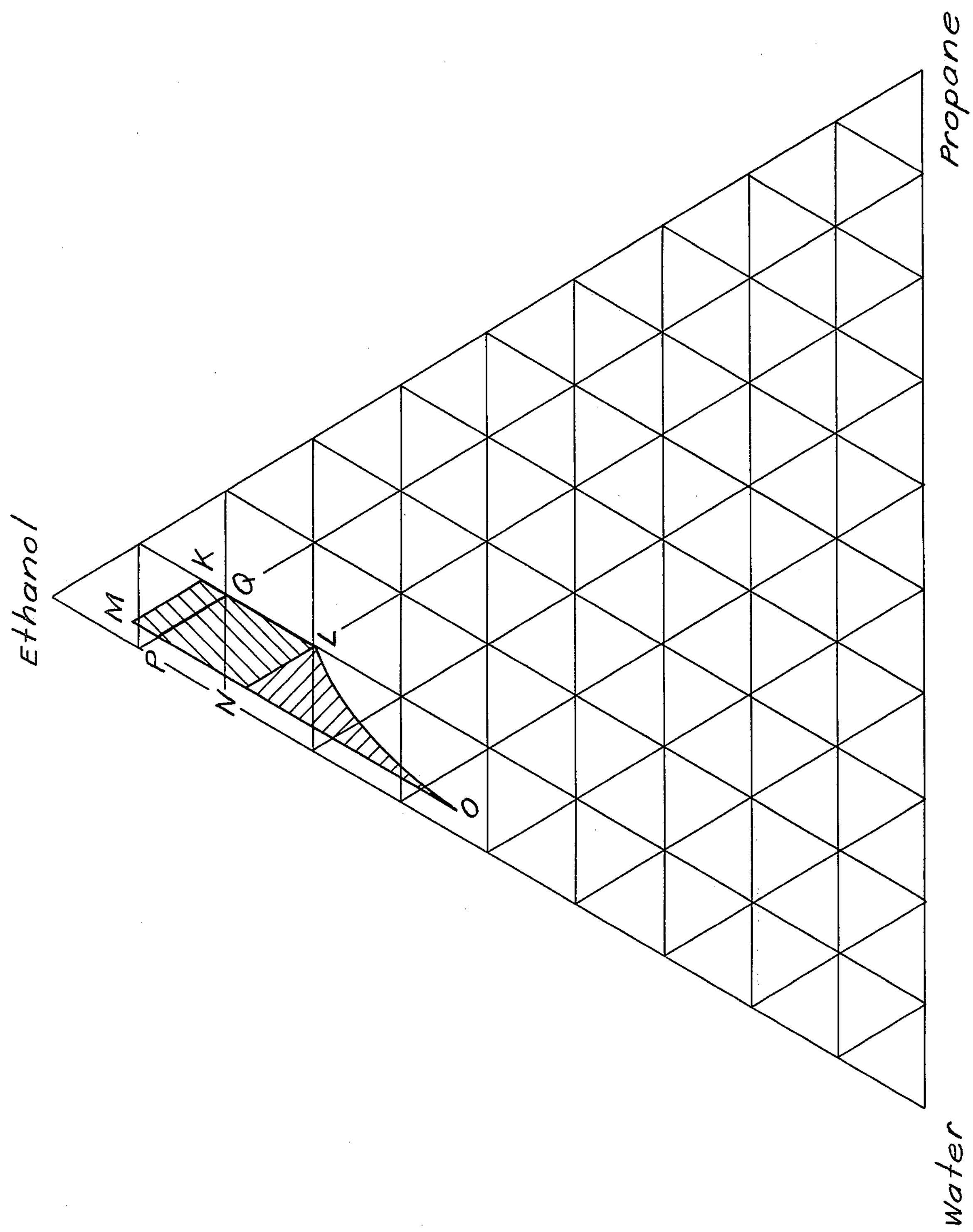
Ethanol
Propane
Water
M
K
Q
L
P
N
O

SPRAY DISINFECTANT AEROSOL

REFERENCE TO PRIOR APPLICATION

This application is a continuation-in-part of our co-pending application U.S. Ser. No. 351,210 filed Apr. 16, 1973 which was a continuation-in-part of our application U.S. Ser. No. 323,754 filed Jan. 15, 1973 and both now abandoned.

BACKGROUND OF THE INVENTION

The present invention lies in the provision of a surface disinfectant composition adaptable for use in an aerosol or like pressurized delivery systems. The use of such pressurized spray compositions is known.

Currently the government requires certain specific tests, described later, for a given formulation to be classed as a general disinfectant, a hospital disinfectant, or a disinfectant having residual activity.

THE PRIOR ART

U.S. Pat. No. 3,102,101 describes air deodorant compositions using an aerosol. Patentees indicate that under certain circumstances the use of saturated hydrocarbon propellants in such deodorants may be acceptable.

U.S. Pat. No. 3,282,776 describes a two phase aerosol germicidal composition having a gaseous phase and a stable homogeneous liquid phase, wherein the latter contains certain amounts of water, ethanol, quaternary compound, an amphoteric surfactant and a normally gaseous halogenated hydrocarbon propellant. Patentees indicate that the propellant is unique and that hydrocarbon propellants under certain conditions produce an unsatisfactorily coarse spray.

U.S. Pat. No. 3,287,214 describes a surface disinfectant of five essential components including a germicide, a deodorant, a saturated monohydric aliphatic alcohol, water, and a normally gaseous chlorofluoroalkane propellant. Patentees indicate that liquefied lower alkanes, such as propane, cannot be used because of the deleterious properties which they would impart to the composition.

SUMMARY OF THE INVENTION

The present invention is a pressurized single phase disinfectant composition consisting essentially of ethanol, water and a propane propellant all within certain critical limits. The compositions find use as a multipurpose surface disinfectant.

The useful compositions are restricted to those falling within the area MKLO of the attached graph, advantageously those within the area PQLN and preferably those within the area LNO. Within those limits the compositions meet the various governmental and commercial requirements.

The ratio of the three indicated ingredients is critical in meeting solubility and germicidal requirements as well as restrictions on flammability and vapor pressure as proscribed by governmental regulations.

As the amount of alcohol is increased beyond the indicated upper limit the compositions tend to become extremely flammable (as defined by the Federal Hazardous Substances Labeling Act). The amount of water at the upper alcohol limit seems to be a minimum amount necessary to attainment of useful germicidal activity. Below the indicated minimum amount of alcohol of about 53 percent will result in unacceptable reduction in solubility of the propellant with consequent unacceptable pressures. The compositions within the preferred area LNO are most satisfactory in meeting the requirements particularly as regards the flammability restrictions. Within the area PQLN the compositions are reliable disinfectants as later defined but exhibit some flammability to an extent requiring labeling to that effect but not to the extent to prevent commercial exploitation if so labeled. The compositions within the area MKQP are reliable against most organisms although not all. For example, those compositions are not classed as reliable in disinfection to *Staphylococcus aureus.* Also within the area MKQP the compositions show the flammability of those within the area PQLN.

The propellant is propane which provides useful vapor pressure for discharging the liquid contents of the pressurized container at a low enough concentration to be soluble in the ethanol-water and to provide a useful spray pattern but not to impart damaging flammability or excessive pressure to the composition. Other hydrocarbons, such as butane and isobutane as well as the higher homologs, require a concentration to achieve a suitable pressure for discharging the contents into a useful spray pattern that is so high as to exceed the solubility limits of the propellant in the alcohol/water solvent. Such multiphase systems require special discharge mechanisms to attain the desired result and, even then, present severe potential flammability problems.

Other propellants that have been used include the halocarbons, such as the chlorofluorocarbons. Those propellants are expensive, are alleged to affect the ecology adversely, decompose in the presence of water, thus adversely affecting odorants and colorants, and require such a high concentration to achieve the desired spray pattern and particle size that the proportion of active ingredients must be adjusted and in so doing the germicidal properties are affected.

Other ingredients may be added to the formulations including deodorants, such as d-limonene, corrosion inhibitors, such as sodium nitrite and such other materials as well make the composition more acceptable to the consumer. Also, additional germicides such as o-phenylphenol may be incorporated into the formulation for residual germicidal effects. In the instance of any additive it must be soluble in the ethanol-water-propane solution to maintain the single phase and it must not detract from the beneficial characteristics of that system.

The production of the compositions is effected by forming a solution of all the ingredients of the liquid phase. That solution is then placed in an aerosol can which has a valve crimped on and the propane added. The can should be agitated to be certain that the propane is solubilized. In a typical multicomponent formulation sodium nitrite would be dissolved in water followed by the ethanol and then d-limonene. Orthophenylphenol is next added and the pH adjusted with caustic. That solution would be placed in the aerosol can and the propane added.

As noted above, the practice of this invention contemplates the use of a conventional aerosol technology.

EXAMPLE 1

Various formulations were prepared from 3.6 weight percent d-limonene, 0.24 weight percent sodium nitrite, 0.12 weight percent o-phenylphenol, 25.94 weight percent deionized water and 66.6 weight percent ethanol (alcohol/water ratio equals 2.59). The formulations were placed in pressurized containers and various levels of propane added. The formulations were tested according to Revised Flammability Test Methods For Aerosol Products (CSMA-Aerosol Guide, Sixth Edition, 1971). The test for flame projection is as follows: The results of testing the formulations are shown in Table I.

The test equipment consists of a base 8 inches wide, 2 feet long, marked in 6 inch intervals. A rule 2 feet long and marked in inches is supported horizontally on the side of the base and about 6 inches above it. A paraffin candle approximately 1 inch in diameter and of such height that the top third of the flame is at the height of the horizontal rule, is placed at the zero point in the base.

The test is conducted in a draft-free area that can be ventilated and cleared after each test. Condition the dispenser to 70° F.±1° F. Shake the dispenser before test. Hold the dispenser upright unless label states otherwise. Place the dispenser at a distance of 6 inches from the flame source. Spray for 4 seconds (one observer noting the extension of the flame and the other operating the dispenser) through the top third of the flame and essentially parallel to the rule. The height of flame should be approximately 2 inches. The normal bending of the flame is part of the recorded distance. Take 3 readings for each test and average. The distance is reported as flame extension.

If during the test the flame travels back the projecting stream to burn at the nozzle of the dispenser it is reported as flashback.

If the flame continues to burn after the product is taken therefrom, it is reported as blowtorch effect.

TABLE I

| | % Propane | | |
|---|---|---|---|
| | 2.5 | 3.5 | 4.5 |
| Flame extension (inches) | 12–15 | 12–15 | 12–15 |
| Flashback | None | None | None |
| Blowtorch Characteristics | None | None | None |

When the same formulation except for replacing propane with 20 weight percent dichloro difluoro methane the flame extension was 15 inches with no flashback or blowtorch effect.

EXAMPLE 2

Spray disinfectants are classified as economic poisons by the government and as such must be registered with the Environmental Protection Agency before they can be sold in interstate commerce. In order to receive E. P. A. registration as a general disinfectant, the following microbiological tests must be passed:

The test method is method (7) Germicidal Spray Products found in Official Methods of Analysis of the Association of Official Analytical Chemists, Eleventh Edition (1970).

1. *Salmonella choleraesuis*—Each of 3 batches must pass 60 slides of 60 that are tested. After 60 days' shelf life, 2 batches must pass 30 slides of 30 tested.

2. *Staphylococcus aureus*—Each of 3 batches must pass 30 slides of 30 tested.

In addition, one other organism of choice must be passed. In this case, the following was chosen.

3. *Trichophyton interdigitale*—Each of 3 batches must pass 30 slides of 30 tested.

4. If a claim to activity against *Streptococcus pyogenes* is to be made, one batch must pass 10 slides of 10 tested.

To be classed as a "Hospital Disinfectant" requires more stringent testing than does the General Disinfectant claim. For hospital disinfectants, *Staphylococcus aureus* is the primary organism, and the additional tests are as follows:

1. *Staphylococcus aureus*—Each of 3 batches must pass 60 slides of 60 tested. After 60 days' shelf life, 2 batches must pass 30 slides of 30 tested.

2. *Pseudomonas aeruginosa*—Each of 3 batches must pass 30 slides of 30 tested.

In addition to these tests, a residual activity test against *Salmonella choleraesuis* must also be passed if residual action is being claimed.

When the formulation of Example 1 containing 3.5 percent propane was subjected to all the above tests, it passed all of them.

Also, efficacy against mold and mildew must be exhibited if activity is to be claimed.

In this regard, the formulation with 3.5 percent propane gave 100 percent protection for one week against mold and mildew on ceramic and fabric substrates. A 41 percent reduction on leather was shown. There was no significant reduction on wood.

EXAMPLE 3

Compositions of various ratios of water, ethanol and propane were packaged in aerosol containers. The compositions were tested according to the procedures identified in Example 2 using only *Staphylococcus aureus* as the organism. The results are shown in Table II.

TABLE II

| Composition | | | Pressure | Disinfection Staph Aureus |
|---|---|---|---|---|
| % Water | % Ethanol | % Propane | PSIG at 70° F. | Tubes Kill/ Tubes Tested |
| This Invention | | | | |
| 10.3 | 83.7 | 6 | 62 | 30/30 |
| 16 | 78.0 | 6 | 65 | 30/30 |
| 34.3 | 62.7 | 3 | 87 | 30/30 |
| 20 | 70 | 10 | 102 | 30/30 |
| 20 | 78 | 2 | 40 | 30/30 |
| 44 | 54 | 2 | 62 | 30/30 |
| 9.6 | 86.9 | 3.5 | 40 | 17/20 |
| 8.8 | 87.7 | 3.5 | <40 | 14/20 |
| 8 | 88.5 | 3.5 | " | 13/20 |
| 7.4 | 89.1 | 3.5 | " | 14/20 |
| 6.9 | 89.6 | 3.5 | " | 1/20 |
| 6.4 | 90.1 | 3.5 | " | 2/20 |
| 6.0 | 90.5 | 3.5 | " | 2/20 |
| 5.6 | 90.9 | 3.5 | " | 1/20 |
| 5.5 | 91.0 | 3.5 | " | 2/20 |
| 5.3 | 91.2 | 3.5 | " | 0/20 |

All of the above pressures fall within the exemptions to the D.O.T. regulations for packaging and shipping compressed gases. Compositions containing 5 and 5.2 percent water gave such erratic results as to be classed as unreliable.

Other compositions were prepared containing greater amounts of propane than that called for in this invention. A composition of 25 percent propane, 60 percent alcohol and 15 percent water exhibited a pressure at 70° F. of 128 psig. A similar composition of 40 percent propane, 50 percent alcohol and 10 percent water had a pressure of 124 psig. The pressures of both of those compositions are such as would require specially constructed D.O.T. 2 Q containers to meet existing regulations.

In contrast the above noted compositions of this invention fall within the scope of the exemptions to those regulations and thus can be packaged in conventional lightweight aerosol cans of 2 P or nonspecified construction.

What is claimed is:

1. A pressurized single phase disinfectant composition consisting essentially of from 7 to 45 weight percent water and from 53 to 91 weight percent ethanol the balance being propane all compositions restricted to those falling within the area MKLO of the accompanying graph.

2. The disinfectant composition of claim 1 wherein said composition is restricted to those falling within the area LNO of the accompanying graph.

3. The disinfectant composition of claim 1 wherein said composition is restricted to those falling within the area PQLN of the accompanying graph.

4. The disinfectant composition of claim 1 containing in addition an odor destroying amount of a deodorant soluble in said composition.

5. The disinfectant composition of claim 4 wherein said deodorant perfume is d-limonene.

6. The disinfectant composition of claim 1 containing in addition a corrosion inhibiting amount of a soluble corrosion inhibitor.

7. The disinfectant composition of claim 6 wherein said corrosion inhibitor is sodium nitrite.

8. The disinfectant composition of claim 1 containing in addition soluble antimicrobial.

9. The disinfectant composition of claim 8 wherein said antimicrobial is o-phenylphenol.

10. The disinfectant composition of claim 1 containing in addition a soluble perfume.

11. A pressurized disinfectant single phase composition consisting of ethanol, water and propane in amounts falling within area LNO of the accompanying graph and a deodorant, a corrosion inhibitor, a perfume and an organic antimicrobial.

* * * * *